(12) United States Patent
Colijn et al.

(10) Patent No.: US 10,336,671 B2
(45) Date of Patent: Jul. 2, 2019

(54) PROCESS FOR RECOVERING A METALLIC COMPONENT

(71) Applicant: SHELL OIL COMPANY, Houston, TX (US)

(72) Inventors: Hendrik Albertus Colijn, Amsterdam (NL); Dionysius Jacobus Maria De Vlieger, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/757,449

(22) PCT Filed: Sep. 5, 2016

(86) PCT No.: PCT/EP2016/070857
§ 371 (c)(1),
(2) Date: Mar. 5, 2018

(87) PCT Pub. No.: WO2017/042125
PCT Pub. Date: Mar. 16, 2017

(65) Prior Publication Data
US 2018/0244594 A1     Aug. 30, 2018

(30) Foreign Application Priority Data

Sep. 7, 2015   (EP) .................................. 15184082

(51) Int. Cl.
*C07C 29/132*   (2006.01)
*C07C 29/145*   (2006.01)
(Continued)

(52) U.S. Cl.
CPC ............. *C07C 29/132* (2013.01); *B01J 23/24* (2013.01); *B01J 23/30* (2013.01); *B01J 25/02* (2013.01); *C07C 29/145* (2013.01); *C22B 7/009* (2013.01); *B01J 23/42* (2013.01); *B01J 23/44* (2013.01); *B01J 23/46* (2013.01); *B01J 23/74* (2013.01); *Y02P 10/214* (2015.11); *Y02P 20/52* (2015.11)

(58) Field of Classification Search
CPC ...... C07C 29/132; C07C 29/145; B01J 23/24; B01J 23/30; B01J 23/42; B01J 23/44; B01J 23/46; B01J 23/74; B01J 23/75; B01J 23/755; B01J 25/02
See application file for complete search history.

(56) References Cited

U.S. PATENT DOCUMENTS 4,417,972 A    11/1983   Francis et al.
4,473,459 A     9/1984   Bose et al.

FOREIGN PATENT DOCUMENTS

CN   102675045 A   9/2012
EP    2348136 A1   7/2011
(Continued)

OTHER PUBLICATIONS

Habainy et al., "Oxidation of Pure Tungsten in the Temperature Interval 400° to 900°C", Master's Thesis, Lund University, European Spallation Source, Sep. 2013, 271 pages.
(Continued)

*Primary Examiner* — Yate' K Cutliff

(57) ABSTRACT

A process for recovering a metallic component from a hydrocarbon product stream is disclosed. The hydrocarbon product stream is subjected to a thermal oxidation. A process for preparing glycols from a saccharide-containing feedstock is additionally disclosed.

9 Claims, 2 Drawing Sheets

(51) Int. Cl.
*B01J 23/24* (2006.01)
*C22B 7/00* (2006.01)
*B01J 23/30* (2006.01)
*B01J 25/02* (2006.01)
B01J 23/42 (2006.01)
B01J 23/46 (2006.01)
B01J 23/74 (2006.01)
B01J 23/44 (2006.01)

(56) References Cited

FOREIGN PATENT DOCUMENTS

| | | | |
|---|---|---|---|
| GB | 2478332 | A | 9/2011 |
| WO | 2013015955 | A2 | 1/2013 |
| WO | 2015028398 | A1 | 3/2015 |
| WO | 2015097096 | A1 | 7/2015 |

OTHER PUBLICATIONS

Na et al., "Direct Catalytic Conversion of Cellulose into Ethylene Glycol Using Nickel-Promoted Tungsten Carbide Catalysts", Angewandte Chemie Int. Ed., vol. 47, Issue 44, Oct. 20, 2008, pp. 8510-8513.
Wang et al., "One-pot conversion of cellulose to ethylene glycol with multifunctional tungsten-based catalysts.", Acc. Chem. Res., vol. 46, No. 7, Feb. 19, 2013, pp. 1377-1386.
International Search Report and Written Opinion received for PCT Patent Application No. PCT/EP2016/070857, dated Feb. 13, 2017, 15 pages.
Lassner et al., "Properties, Chemistry, Technology of the Element, Alloys, and Chemical Compounds", Tungsten, 1999, 447 pages.

PROCESS FOR RECOVERING A METALLIC COMPONENT

PRIORITY CLAIM

The present application is the National Stage (§ 371) of International Application No. PCT/EP2016/070857, filed 5 Sep. 2016, which claims priority from European Application No. 15184082.4, filed 7 Sep. 2015 incorporated herein by reference.

FIELD OF THE INVENTION

The present invention relates to a process for recovering a metallic component from a hydrocarbon stream and to a process for preparing glycols from a saccharide-containing feedstock.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. The conversion of sugars to glycols can be seen as an efficient use of the starting materials with the oxygen atoms remaining intact in the desired product.

Current methods for the conversion of saccharides to sugars revolve around a hydrogenation/hydrogenolysis process as described in Angew. Chem. Int. Ed. 2008, 47, 8510-8513.

WO 2015028398 describes a continuous process for the conversion of a saccharide-containing feedstock into glycols. In this process the saccharide-containing feedstock is contacted in a reactor with a catalyst composition comprising at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof. The second active catalyst component may be present in homogeneous form.

Homogeneous catalysts are typically recycled to the reactor as components of a stream that is withdrawn from the reactor and partially returned to the reactor. The stream consists mainly of heavy hydrocarbon products that are formed in the glycol production process, e.g. the stream may comprise $C^{3+}$ sugar alcohols and carboxylic acids. This stream will potentially also contain buffer components that are used in the reactor to maintain the pH (a preferred range is from 4 to 6). A bleed stream is applied to the recycle to prevent build-up of inerts and contaminants in the process. The bleed stream may be disposed of via flaring. This flaring typically destroys homogeneous catalysts that are present in the bleed stream, and can lead to release of metal-containing gases into the environment.

The present inventors have sought to provide a process wherein metallic components (typically the homogeneous catalyst and any buffer components that are present) may be recovered from the hydrocarbon bleed stream produced in the process for the production of glycols. Recovery of such components would enable further use of the metal and would also help to avoid release of emissions resulting from the metallic components.

SUMMARY OF THE INVENTION

Accordingly, the present invention provides a process for recovering a metallic component from a hydrocarbon product stream comprising steps of:
(a) subjecting the hydrocarbon product stream to a thermal oxidation at a temperature of from 300 to 750° C., thereby providing a solid residue; and
(b) collecting the solid residue.

Recovery of any metallic components, particularly any catalyst components, is economically and environmentally advantageous. The inventors have found that this process can be used to recover metallic components from the hydrocarbon bleed stream that results from a process for the production of glycols from saccharide feedstock. Accordingly the present invention further provides a process for preparing glycols from a saccharide-containing feedstock comprising steps of:
(i) providing a saccharide-containing feedstock, water and hydrogen to a reactor, wherein the reactor contains at least two active catalytic components, said active catalyst components comprising, as a first active catalyst component, one or more materials selected from transition metals from groups 8, 9 or 10 or compounds thereof, with catalytic hydrogenation capabilities; and, as a second active catalyst component, one or more homogeneous catalysts selected from tungsten, molybdenum, lanthanum, tin or compounds or complexes thereof;
(ii) withdrawing a reactor product stream from the reactor;
(iii) separating the reactor product stream into at least a glycol product stream and a hydrocarbon heavies stream, wherein the hydrocarbon heavies stream is at least partially recycled back to the reactor;
(iv) bleeding a hydrocarbon product stream from the hydrocarbon heavies stream as it is recycled to the reactor;
(v) subjecting the hydrocarbon product stream to a thermal oxidation at a temperature of from 300 to 750° C., thereby providing a solid residue; and
(vi) collecting the solid residue.

A bleed stream is typically used to prevent accumulation of heavy components that cannot be broken down to provide glycols. The bleed stream also removes and thereby prevents build-up of pollutants that may be present in the saccharide-containing feedstock. In the process of the present invention, the metallic components from the bleed stream (typically homogeneous catalyst components and buffer components) are recovered by carrying out a controlled thermal oxidation and collecting the resulting solid residue. The metallic components may be reused and emissions due to combustion of the metallic components are avoided.

DETAILED DESCRIPTION OF THE INVENTION

Figure 1:
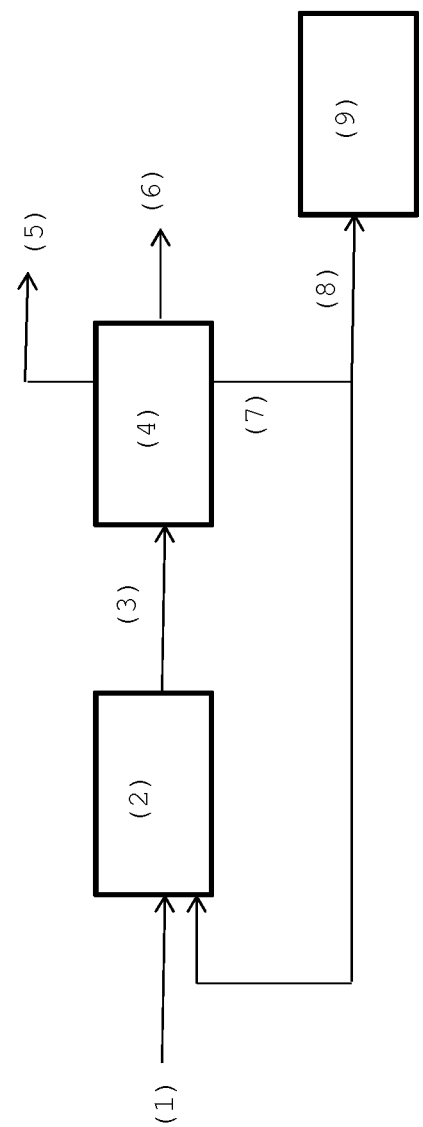
FIG. 1 shows an example of a process according to the invention wherein glycols are prepared from a saccharide-containing feedstock.

In the process of the present invention one or more metallic components are recovered from a hydrocarbon product stream. In this description the term "hydrocarbon" is used to cover not only chemical species that are composed only of hydrogen and carbon, but also to cover chemical species that are composed of hydrogen, carbon and oxygen. Oxygenates such as sugars, sugar alcohols, alcohols, diols and carboxylic acids are considered to be "hydrocarbon" compounds for the purposes of the present invention. Preferably the hydrocarbon product stream is at least 80 wt % hydrocarbon, more preferably at least 90 wt % hydrocarbon. The hydrocarbon product stream comprises a metallic component that may suitably be a metallic homogeneous catalyst, the degradation products that can result when such a metallic catalyst degrades, or a metallic buffer component. The metallic component in the hydrocarbon product stream suitably comprises one or more compound, complex or elemental material comprising tungsten, molybdenum, lanthanum or tin. Preferably, the metallic component comprises one or more compound, complex or elemental material selected from those containing tungsten or molybdenum. More preferably, the metallic component comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides and combinations thereof. Most preferably the metallic component comprises sodium metatungstate.

If the metallic component has resulted (at least in part) from a buffer (e.g. sodium bicarbonate), it typically will comprise an alkaline metal such as sodium.

The hydrocarbon product stream typically comprises from 0.1 to 20 wt % of metallic components, based upon the weight of the metal compared to the weight of the hydrocarbon product stream, preferably from 2 to 18 wt %, more preferably from 5 to 15 wt %.

The hydrocarbon product stream is subjected to a thermal oxidation at a temperature of from 300 to 750° C. During the thermal oxidation the hydrocarbons that are present in the hydrocarbon product stream are combusted, thus providing gaseous carbon dioxide and water. Inorganic components that were dissolved in the hydrocarbon product stream will remain as a solid residue. It is important that the temperature of the thermal oxidation is below 750° C. as metallic components such as tungsten start to volatilise at 750° C. (see the discussion on page 86 of Tungsten: Properties, Chemistry, Technology of the Element, Alloys and Chemical Compounds by Erik Lassner and Wolf-Dieter Schubert). This is why flaring typically destroys homogeneous catalysts that are present in the bleed stream resulting during the process for preparing glycols from saccharide-containing feedstocks. It is important that the temperature of the thermal oxidation is 300° C. or above as this is sufficient to combust the hydrocarbons, thereby transforming them into gaseous components. Additionally a temperature of less than 300° C. may give incomplete oxidation of the organic components leading to deposits of carbonaceous materials.

The temperature of the thermal oxidation is from 300 to 750° C., preferably from 300 to 600° C. and more preferably from 350 to 500° C. A temperature of less than 500° C. is preferred as higher temperatures will require higher energy input, and also because the inventors have observed that some evaporation of materials such as tungsten may occur between 500 and 750° C.

The thermal oxidation preferably takes place at atmospheric pressure. The thermal oxidation preferably takes place in air, but oxygen could also be supplied.

Suitably a multiple oven system is used to carry out the thermal oxidation. The hydrocarbon product stream is suitably supplied to a first oven in the multiple oven system and then, after a period of time, the hydrocarbon stream is supplied to a second oven in the multiple oven system. Whilst the hydrocarbon stream is supplied to the second oven the solid residue can be collected from the first oven. After a further period of time the hydrocarbon stream may be supplied again to the first oven so that the solid residue can be collected from the second oven. Having such a swing system wherein the hydrocarbon product stream may be redirected to different ovens enables the solid residue to be collected without stopping the process.

The solid residue may be collected in solid form, or it may be dissolved in a solvent, thereby providing a solution that can be subjected to further processing. Dissolving the solid residue in a solvent may be preferred if the solid residue comprises carbonaceous deposits in addition to the metallic component. Carbonaceous deposits may be present in the solid residue if there has been incomplete combustion of the hydrocarbons and these will not dissolve in the solvent, allowing for separation of the carbonaceous deposits by filtration. The metallic component that will be present in the solid residue (or a solution thereof) may require reactivation. In a preferred embodiment of the invention the metallic component that is recovered is an active catalyst component (and does not require reactivation) and it can be dissolved in a process stream and recycled back to a process for preparing glycols.

The invention provides a process for preparing glycols from a saccharide-containing feedstock. The saccharide-containing feedstock preferably comprises starch. It may also comprise one or more further saccharide selected from the group consisting of monosaccharides, disaccharides, oligosaccharides and polysaccharides other than starch. Examples of polysaccharides other than starch include cellulose, hemicelluloses, glycogen, chitin and mixtures thereof.

The saccharide-containing feedstock may be derived from grains such as corn, wheat, millet, oats, rye, sorghum, barley or buckwheat, from rice, from pulses such as soybean, pea, chickpea or lentil, from bananas and/or from root vegetables such as potato, yam, sweet potato, cassava and sugar beet, or any combinations thereof. A preferred source of saccharide-containing feedstock is corn.

The saccharide-containing feedstock, water and hydrogen are supplied to a reactor. Suitably the ratio of saccharide-containing feedstock and water are adjusted such that the reactor feedstock contains water:saccharide in a ratio of between 1:1 and 5:1. The hydrogen pressure is suitably greater than 10 bar, preferably greater than 70 bar and most preferably around 100 bar. The amount of hydrogen consumed will depend upon the amount of saccharide that is provided (1 mole of glucose will react with 3 moles of hydrogen).

The reactor contains at least two active catalytic components, said active catalyst components comprising, as a first active catalyst component, one or more materials selected from transition metals from groups 8, 9 or 10 or compounds thereof, with catalytic hydrogenation capabilities; and, as a second active catalyst component, one or more homogeneous catalysts selected from tungsten, molybdenum, lanthanum, tin or compounds or complexes thereof. The second active catalyst component functions as a retro-aldol catalyst, selectively cutting the saccharide molecules into smaller components. The first active catalyst component acts as a hydrogenation catalyst.

The first active catalyst component is suitably a heterogeneous catalyst. When the first active catalyst component is heterogeneous there will not be significant quantities of metal from the first active catalyst component in the hydrocarbon product stream, although it is possible that there might be very low levels of metal (e.g. up to 10 ppm) that has leached from the heterogeneous catalyst that are found in the hydrocarbon product stream. The second active catalyst component is a homogeneous catalyst so the hydrocarbon product stream will contain one or more metallic components that are either the homogeneous catalyst or degradation products resulting from the homogeneous catalyst.

Suitably, the first active catalyst component consists of one or more of the group selected from iron, cobalt, nickel, ruthenium, rhodium, palladium, iridium and platinum. This component may be present in the elemental form or as a compound. A preferred catalyst is Raney nickel. Another possible catalyst is ruthenium dispersed on carbon.

The second active catalyst component preferably comprises one or more homogeneous catalysts selected from tungsten or molybdenum, or compounds or complexes thereof. Most preferably, the second active catalyst comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides and combinations thereof.

A buffer is preferably supplied to the reactor. The purpose of the buffer is to maintain the pH of the reactor in a preferred range. Suitable buffers will be known to the skilled person but include sodium bicarbonate. The amount of buffer supplied to the reactor is suitably from 0.05 to 5 wt % of buffer based on the total weight of feedstock supplied to the reactor, preferably from 0.1 to 1 wt % of buffer. If a buffer is used the hydrocarbon product stream will contain a metallic component resulting from the buffer and this can be recovered in the process of the present invention.

The feedstock, hydrogen and water are supplied to the reactor. Additional reactors may be present downstream of the reactor. Suitably reaction conditions, particularly temperature and pressure, can be varied between the reactors if additional reactors are used.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the reactor is heated to a temperature within these limits before addition of any starting material and is maintained at such a temperature as the reaction proceeds.

The pressure in the reactor is suitably at least 1 MPa, preferably at least 2 MPa, more preferably at least 3 MPa. The pressure in the reactor is suitably at most 15 MPa, preferably at most 12 MPa, more preferably at most 10 MPa, most preferably at most 8 MPa. Preferably, the reactor is pressurised to a pressure within these limits by addition of hydrogen before addition of any saccharide-containing feedstock or water and is maintained at such a pressure as the reaction proceeds through on-going addition of hydrogen.

The process takes place in the presence of hydrogen. Preferably, the process takes place in the absence of air or oxygen. In order to achieve this, it is preferable that the atmosphere in the reactor be evacuated and replaced an inert gas, such as nitrogen, and then with hydrogen repeatedly, after loading of any initial reactor contents, before the reaction starts.

Suitable reactors include stirred tank reactors, slurry reactors, ebulated bed reactors, jet flow reactors, mechanically agitated reactors, bubble columns, such as slurry bubble columns and external recycle loop reactors. The use of these reactors allows dilution of the reaction feedstock and intermediates to an extent that provides high degrees of selectivity to the desired glycol product (mainly ethylene and propylene glycols), such as by effective back-mixing.

The residence time in the reactor is suitably at least 1 minute, preferably at least 2 minutes, more preferably at least 5 minutes. Suitably the residence time in the reactor is no more than 5 hours, preferably no more than 2 hours, more preferably no more than 1 hour.

A reactor product stream is withdrawn from the reactor. Typically this stream contains water, hydrocarbons, homogeneous catalyst and buffer (if used). The reactor product stream is separated into at least a glycol product stream and a hydrocarbon heavies stream. Preferably the reactor product stream is additionally separated into a light hydrocarbon stream and water. In a preferred separation step, the light hydrocarbon stream first separated from the reactor product stream and then the water is removed by distillation. The glycol product stream is then separated from the hydrocarbon heavies stream by distillation (the hydrocarbon heavies stream is the bottom product from this distillation).

The glycol product stream comprises as least one of monoethylene glycol (MEG), monopropylene glycol (MPG) and 1,2-butanediol (1,2-BDO). The different glycols may be collected as separate streams or as one combined stream.

A hydrocarbon heavies stream is separated from the reactor product stream, and is at least partially recycled back to the reactor, either directly or indirectly. The hydrocarbon heavies stream typically contains heavy hydrocarbons, the second active catalyst component and the buffer (if used). The recycling of this stream enables reuse of the homogeneous second active catalyst component.

A hydrocarbon product stream is bled from the hydrocarbon heavies stream as it is recycled to the reactor. In this context, "bleeding" means removing small quantities of material from the recycle on a regular basis. Suitably from 1 to 20 wt % and preferably around 10 wt % of the hydrocarbon heavies stream is bled to provide the hydrocarbon product stream. This is suitably done on a continuous basis by splitting the hydrocarbon heavies stream into a minor stream (which becomes the hydrocarbon product stream) and a major stream (which is recycled to the reactor).

The hydrocarbon product stream is subjected to a thermal oxidation at a temperature of from 300 to 750° C., thereby providing a solid residue. The temperature of the thermal oxidation is from 300 to 750° C., preferably from 300 to 600° C. and more preferably from 350 to 500° C. The thermal oxidation preferably takes place at atmospheric pressure. The thermal oxidation preferably takes place in air, but oxygen could also be supplied. Suitably a multiple oven system (as described above) is used to carry out the thermal oxidation.

The solid residue may be collected in solid form, or it may be dissolved in a solvent, thereby providing a solution that can be subjected to further processing. Suitably the solution is filtered to allow for separation of carbonaceous deposits that may have been present in the solid residue if there has been incomplete combustion of the hydrocarbons (such carbonaceous deposits will not dissolve in the solvent). The solvent may be an aqueous solvent such as water or an aqueous stream originating from the process for preparing glycols from the saccharide-containing feedstock. The solvent may alternatively be a hydrocarbon solvent (wherein the term hydrocarbon includes oxygenates such as glycols), such as a hydrocarbon stream originating from the process for preparing glycols from the saccharide-containing feedstock.

FIG. 1 shows an example of a process according to the invention wherein glycols are prepared from a saccharide-containing feedstock. A saccharide-containing feedstock, water, hydrogen, a homogeneous retro-aldol catalyst and a buffer are fed (1) to a reactor (2). The reactor (2) contains two active catalytic components, specifically a heterogeneous hydrogenation catalyst and the homogeneous retro-aldol catalyst. The saccharide-containing feedstock reacts to provide glycols. A reactor product stream (3) from the reactor (2) is provided to a separator (4). Water (5) is withdrawn from the separator (4). A glycols product stream (6) is withdrawn from the separator (4). A hydrocarbon heavies stream (7) is withdrawn from the separator (4) and is recycled to the reactor (2). A hydrocarbon product stream (8) is bled from the hydrocarbon heavies stream (7) and is supplied to an oven (9). In the oven (9) the hydrocarbon product stream (8) is subjected to a thermal oxidation at a temperature of from 300 to 750° C. A solid residue is collected from the oven (9).

Figure 2:
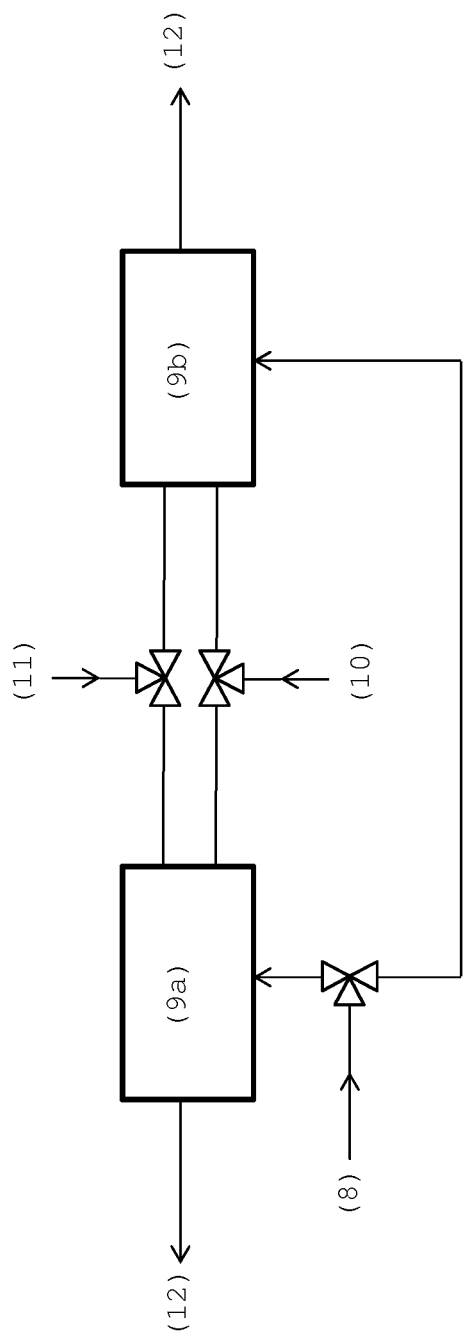
FIG. 2 shows an example of a multiple oven system that can be used in the process of the present invention.

FIG. 2 shows an example of a multiple oven system that can be used in the present invention. The hydrocarbon product stream (8) is supplied to either a first oven (9a) or a second oven (9b) via valves that can direct the flow. Hot air (10) is supplied to the ovens (9a, 9b) via valves to heat the hydrocarbon product stream in the ovens. Solvent (11), which is typically a product stream from the glycol production process, is supplied to the ovens (9a, 9b) via valves to collect the solid residue. A solution or dispersion (12) of the solid residue is collected from both ovens. This apparatus enables continuous processing of the hydrocarbon product stream (8). The hydrocarbon product stream (8) and hot air (10) can be supplied to the first oven (9a) such that thermal oxidation takes place in the first oven. Then the valves can be switched such that the hydrocarbon product stream (8) and hot air (10) are supplied to the second oven (9b) such that thermal oxidation takes place in the second oven. Solvent (11) can then be supplied to the first oven (9a) such that the solid residue in the first oven is dissolved or dispersed and withdrawn as a solution or dispersion (12) from the first oven (9a). The valves can then be switched again such that the hydrocarbon product stream (8) and hot air (10) are again supplied to the first oven (9a), solvent (11) is supplied to the second oven (9b), and a solution or dispersion (12) is withdrawn from the second oven (9b).

The present invention is further illustrated in the following Example.

EXAMPLE

A heavy stream was withdrawn from a process for preparing glycols from a saccharide-containing feedstock. The reactor contained a Raney nickel hydrogenation catalyst, a sodium metatungstate retro-aldol catalyst and a sodium bicarbonate buffer. The heavy stream contained sodium metatungstate and sodium carbonate. A portion of the heavy stream was heated in an oxygen-containing atmosphere at 450° C.

After heating, a white water-soluble solid was recovered. The solid was found to be $Na_2W_2O_7$ and $Na_2WO_4$. The solid was shown to be soluble in hot water. The recovered catalytic material had comparable catalytic activity to the fresh catalytic material fed into the reactor.

In similar experiments, carbonaceous deposits on the water-soluble solid were observed.

That which is claimed is:

1. A process for preparing glycols from a saccharide-containing feedstock comprising steps of:
   (i) providing a saccharide-containing feedstock, water and hydrogen to a reactor, wherein the reactor contains at least two active catalytic components, said active catalyst components comprising, as a first active catalyst component, one or more materials selected from transition metals from groups 8, 9 or 10 or compounds thereof, with catalytic hydrogenation capabilities; and, as a second active catalyst component, one or more homogeneous catalysts selected from tungsten, molybdenum, lanthanum, tin or compounds or complexes thereof;
   (ii) withdrawing a reactor product stream from the reactor;
   (iii) separating the reactor product stream into at least a glycol product stream and a hydrocarbon heavies stream, wherein the hydrocarbon heavies stream is at least partially recycled back to the reactor;
   (iv) bleeding a hydrocarbon product stream from the hydrocarbon heavies stream as it is recycled to the reactor;
   (v) subjecting the hydrocarbon product stream to a thermal oxidation at a temperature of from 300 to 750° C., thereby providing a solid residue; and
   (vi) collecting the solid residue.

2. A process according to claim 1, wherein the first active catalyst component is a heterogeneous catalyst and consists of one or more of the group selected from iron, cobalt, nickel, ruthenium, rhodium, palladium, iridium and platinum.

3. A process according to claim 1, wherein the second active catalyst component comprises one or more homogeneous catalysts selected from compounds or complexes of tungsten or molybdenum.

4. A process according to claim 3, wherein the second active catalyst comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides and combinations thereof.

5. A process according to claim 1, wherein a buffer is supplied to the reactor.

6. A process according to claim 1, wherein the temperature of the thermal oxidation is from 350 to 500° C.

7. A process according to claim 1, wherein the solid residue is dissolved in a solvent, thereby providing a solution, and wherein the solution is filtered to allow for separation of carbonaceous deposits that may have been present in the solid residue.

8. A process according to claim 7, wherein the solvent is an aqueous stream originating from the process for preparing glycols from the saccharide-containing feedstock.

9. A process according to claim 7, wherein the solvent is a hydrocarbon stream originating from the process for preparing glycols from the saccharide-containing feedstock.

\* \* \* \* \*